(12) United States Patent
Rosen

(10) Patent No.: US 6,640,815 B1
(45) Date of Patent: Nov. 4, 2003

(54) CONSUMER USABLE POPCORN KERNEL AND/OR HUSK REMOVING DENTAL INSTRUMENT

(76) Inventor: Gregory J. Rosen, 3 S. Elberon Sq., Long Branch, NJ (US) 07740

( * ) Notice: Subject to any disclaimer, the term of this patent is extended or adjusted under 35 U.S.C. 154(b) by 0 days.

(21) Appl. No.: 10/224,265

(22) Filed: Aug. 21, 2002

(51) Int. Cl.[7] ............................ A61C 15/00; A61C 3/06
(52) U.S. Cl. .................. 132/321; 132/329; 433/142
(58) Field of Search ................ 132/321, 329; 433/142, 143, 141; D9/305, 337; D7/635; D28/65; 206/368, 63.5

(56) References Cited

U.S. PATENT DOCUMENTS

| | | | | |
|---|---|---|---|---|
| D53,958 S | * | 10/1919 | Zurbrigg | 433/142 |
| 3,101,727 A | * | 8/1963 | Wiseman | 132/321 |
| 3,672,378 A | * | 6/1972 | Silverman | 132/321 |
| 4,271,854 A | * | 6/1981 | Bengtsson | 132/321 |
| 4,781,590 A | * | 11/1988 | Weinstein | 433/142 |
| 4,805,646 A | * | 2/1989 | Shimenkpv | 132/329 |
| 4,832,061 A | * | 5/1989 | Hwang | 132/329 |
| D355,593 S | * | 2/1995 | Bell | D9/305 |
| 5,913,682 A | * | 6/1999 | Strate | 433/143 |
| 6,012,468 A | * | 1/2000 | Huang | 132/321 |
| 6,071,122 A | * | 6/2000 | Kilcher et al. | 433/141 |
| 6,102,051 A | * | 8/2000 | Heves | 132/321 |
| 6,220,258 B1 | * | 4/2001 | Briggs et al. | 132/329 |
| 6,245,367 B1 | * | 6/2001 | Galomb | 426/115 |

* cited by examiner

Primary Examiner—Todd E. Manahan
(74) Attorney, Agent, or Firm—Charles I Brodsky

(57) ABSTRACT

A dental instrument including a plastic handle with a generally planar pick at at least one of its ends, with the pick being of a plastic or emery board composition of given shape and angulation, with a rasped surface about edge portions of the pick so as to fit within a user's mouth on either the inside or outside of the gingiva, in serving as an emergency dental treatment relief device in dislodging popcorn stuck in the teeth.

2 Claims, 3 Drawing Sheets

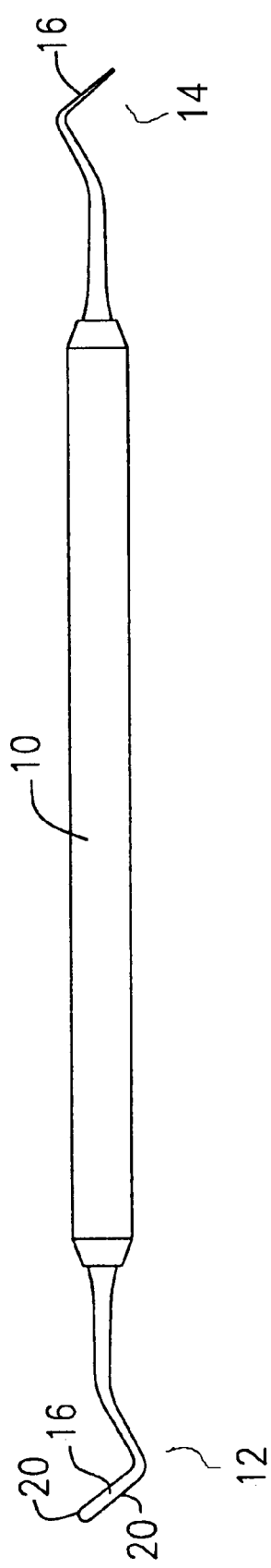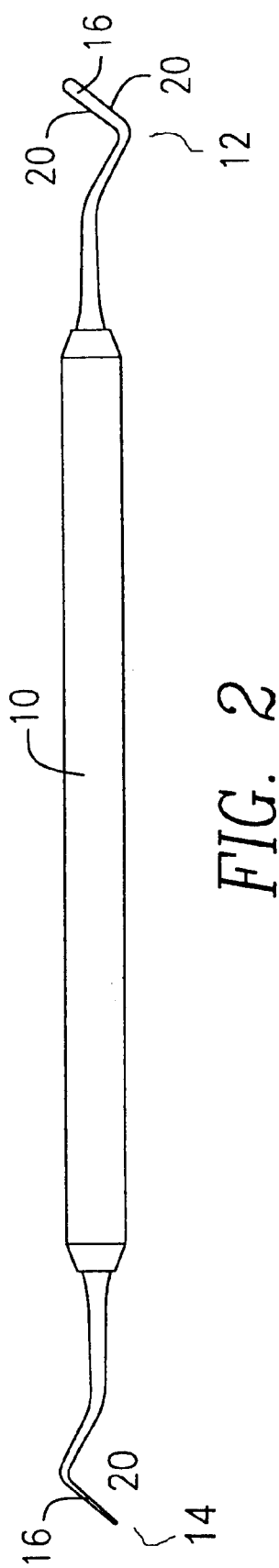

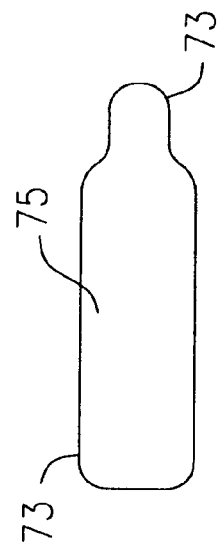
*FIG. 7*
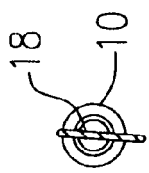
*FIG. 5*
*FIG. 6*

CONSUMER USABLE POPCORN KERNEL AND/OR HUSK REMOVING DENTAL INSTRUMENT

CROSS-REFERENCE TO RELATED APPLICATIONS

NONE

STATEMENT REGARDING FEDERALLY SPONSORED RESEARCH OR DEVELOPMENT

Research and development of this invention and Application have not been federally sponsored, and no rights are given under any Federal program.

REFERENCE TO A MICROFICHE APPENDIX

NOT APPLICABLE

BACKGROUND OF THE INVENTION

1. Field of the Invention

This invention relates to the caring of dental teeth, in general, and to an emergency treatment device for providing at least temporary relief in removing popcorn kernels and/or husks stuck in the teeth, in particular.

2. Description of the Related Art

As is well known and understood, studies document that over 50% of the population do not ever treat with a dentist on a regular basis. Studies also show that even in dental emergencies, large portions of the populace do not seek professional assistance, but attempt to deal with the problem themselves. Even for those who have regular dental appointments, or who seek help when a problem arises, many are the times when seeing a dentist, even on an emergency basis, is not feasible. For such instances, pharmacies oftentimes stock items for emergency treatment by the consumer on an individual basis—until such times as a visit to a dentist could be scheduled. Many times, however, an availability of the dentist to see a patient cannot be arranged conveniently. During such times, the patient continues to suffer discomfort and annoyance—which it would be desirable to eliminate. Investigation and analysis of the situation reveals that one such instance occurs when a popcorn kernel and/or husk is stuck within the consumer's teeth. Generally, there is nothing available on the market to assist such distressed person in circumstances of this kind; and try as one might to dislodge the kernel or husk with the tongue or a finger, its removal, short of finding a dentist to effectuate it, oftentimes presents a formidable task.

SUMMARY OF THE INVENTION

As will become clear from the following description, the present. invention recognizes the desirability of having a dental instrument, simple enough for a consumer to employ himself/herself, and available for purchase in a pharmacy to deal with the stuck kernel and/or husk without the need for having to visit the dentist. As will also be seen, the unique dental instrument of the invention follows the recognition that the treatment cost of a dental visit to resolve this problem might seem out of proportion to the degree of discomfort and annoyance present—and, most probably, a visit that probably would not be covered by any dental insurance that might be available. As will be understood from the description that follows, such a consumer usable dental instrument intended for pharmacy purchase according to the invention includes a plastic handle having first and second opposing ends, along with a generally planar pick at at least one of the ends—the pick being of plastic or emery board composition of given shape and angulation with a rasped surface about its flat edge portions to allow for catching of the kernels or husks, wherever they may be positioned.

In a preferred embodiment, a planar pick having the rasped surface is included with the plastic handle at each of its ends, with the individual picks being of differing angles so as to fit within a user's mouth on either the inside or outside of the gingiva. When included within a blister pack for sale, the dental instrument of the invention becomes readily purchasable from a pharmacy as an emergency treatment device in catching and removing the stuck kernel and/or husk, thereby obviating the need to seek relief from a dentist who might not then be nearby or "on call". As will be appreciated, a consumer usable popcorn kernel and/or husk removing dental instrument of this type could further be included within the blister pack for distribution along with a package of popcorn being sold. Whether the dental instrument includes one or a pair of planar picks, a generally plastic fabrication allows for its sale from a pharmacy as an emergency treatment device for the inexpensive cost of one dollar ($1.00) or so—or even given away for free as a promotional item along with the package of popcorn being sold.

BRIEF DESCRIPTION OF THE DRAWINGS

These and other features of the present invention will be more clearly understood from a consideration of the following description, taken in connection with the accompanying drawings, in which:

FIG. 1 is a front view of the consumer usable popcorn kernel and/or husk removing dental instrument constructed in accordance with the teachings of the invention;

FIG. 2 is a rear view of the dental instrument of FIG. 1;

FIGS. 5 and 6 are right and left side views, respectively, of the popcorn kernel and/or husk removing dental instrument of the invention; and FIG. 7 is a top view helpful in understanding an alternative embodiment of the invention.

DETAILED DESCRIPTION OF THE INVENTION

Figure 3:
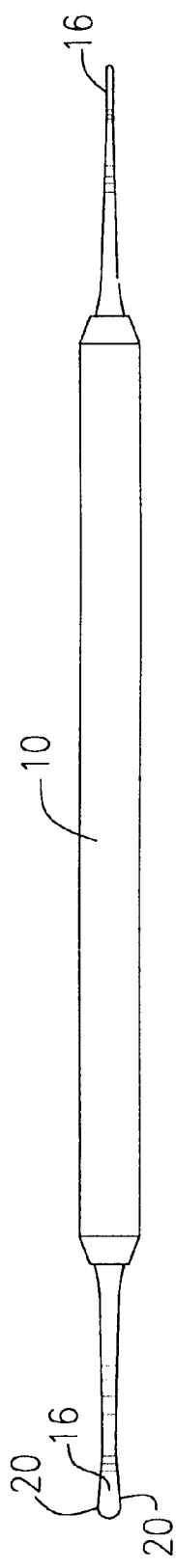
FIGS. 3 and 4 are top and bottom views, respectively, of the dental instrument.
Figure 4:
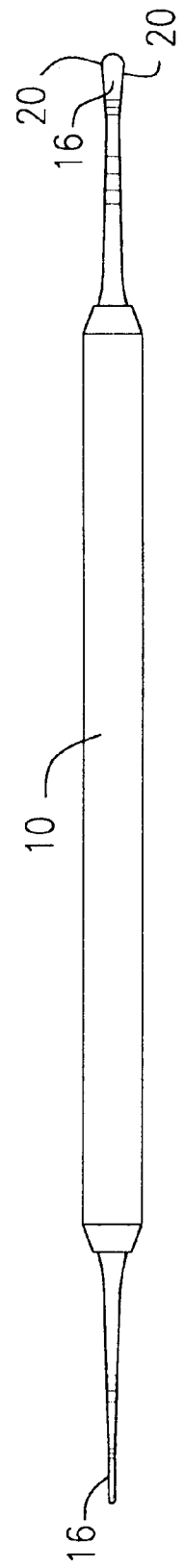

Referring to the drawings, the consumer usable popcorn kernel and/or husk removing dental instrument of the invention comprises a plastic handle 10 having first and second opposing ends 12, 14. A generally planar pick 16, in accordance with the invention, may be secured with one of the two ends, or fabricated there as part of the plastic handle itself—although in the preferred embodiment of the drawings, a pair of picks 16 are included, one at each of the opposing ends 12, 14. Such pick(s) 16 is preferably of a plastic composition, or of an emery board with a paperboard backing composition, of given shape and angulation so as to fit within a user's mouth on either the inside or outside of the gingiva in forming a dental instrument. As illustrated in the various drawings, the two picks 16 are each of differing angles, and each provided with a rasped surface 18 about their flat portions 20. As will be appreciated, such surfaces 18 allow for the catching of any stuck popcorn kernel and/or husk, as an assist in its removal by the user, without having to resort to visiting a dentist to accomplish the task.

By being fabricated with a plastic or emery board pick composition, the consumer usable dental instrument of this type can be fabricated for purchase as an emergency dental treatment relief device for a nominal cost of one dollar ($1.00), or so. Included within a blister pack for such sale, the dental instrument can be obtainable as an emergency treatment relief device from a pharmacy; alternatively, it can be packaged as a promotional item along with a package of popcorn being sold in general. In the event that a kernel and/or its husk becomes caught between one's teeth, the dental instrument of the invention can then easily be manipulated to remove it should its attempted dislodgement by the tongue or fingers prove unsuccessful. An expensive visit to a dentist to remove the discomforting and annoying stuck kernel and/or husk can thus be avoided.

While there have been described what are considered to be preferred embodiments of the present invention, it will be readily appreciated by those skilled in the art that modifications can be made without departing from the scope of the teachings herein. For example, although the planar pick(s) 16 is illustrated in the drawings as being of a particular shape and angulation, other designs and configurations can be had equally as well, as long as the configurations continue to allow the pick(s) to fit within a user's mouth on either the inside or outside of the gingiva in freeing the stuck popcorn. Thus, a shape resembling a silhouette of a bottle with sharp line angles to access hard to reach locations on the gingival margin is particularly desirable, as an aid in removing popcorn kernels embedded in the gingiva (FIG. 7, the sharp line angles being shown at 73 for the bottle shape 75). For at least such reason, therefore, resort should be had to the claims appended hereto for a true understanding of the scope of the invention.

I claim:

1. A consumer usable popcorn kernel and/or husk removing dental instrument, comprising:

a plastic handle having first and second opposing ends;

a first generally planar pick at said first end extending axially of said handle to a first point, then extending downwardly therefrom to a second point, and then extending upwardly therefrom to a third point;

a second generally planar pick at said second end extending axially of said handle to a first point, then extending upwardly therefrom to a second point and then extending downwardly therefrom to a third point;

and with each of said first and second generally planar picks being of one of plastic and emery board composition of given shape and angulation, with a rasped surface about edge flat portions thereof to dislodge a stuck kernel and/or husk by a downward motion and to remove it by an upward motion.

2. The dental instrument of claim 1 wherein each of said first and second generally planar picks extend at differing angles with respect to a longitudinal axis of said handle so as to fit within a user's mouth on either the inside or outside of the gingiva.

* * * * *